United States Patent [19]

Kominek et al.

[11] Patent Number: 4,704,358

[45] Date of Patent: Nov. 3, 1987

[54] $\Delta^1$-DEHYDROGENATION WITH HEAT OR AIR-DRIED B. CYCLOOXIDANS

[75] Inventors: Leo A. Kominek, Portage; Holly J. Wolf, Comstock Township, Kalamazoo County, both of Mich.

[73] Assignee: The Upjohn Company, Kalamazoo, Mich.

[21] Appl. No.: 721,011

[22] Filed: Apr. 8, 1985

Related U.S. Application Data

[63] Continuation of Ser. No. 436,552, Oct. 25, 1982, Pat. No. 4,524,134, which is a continuation-in-part of Ser. No. 403,949, Jul. 30, 1982, abandoned.

[51] Int. Cl.[4] .......................... C12P 33/02; C12N 1/04
[52] U.S. Cl. ........................................ 435/61; 435/260
[58] Field of Search .......................... 435/61, 182, 260

[56] References Cited

U.S. PATENT DOCUMENTS 2,837,464  6/1958  Nobile .................................. 195/51
3,360,439  12/1967  Erickson et al. ...................... 195/51
4,035,236  7/1977  Wovcha ............................... 195/51
4,041,055  8/1977  Shephard et al. ................. 260/397.3

OTHER PUBLICATIONS

Charney, W. & Herzog, H., Microbial Transformation of Steroids, Academic Press, New York, 1967, pp. 4–9, 236–261.

Primary Examiner—Alvin E. Tanenholtz
Attorney, Agent, or Firm—Bruce Stein

[57] ABSTRACT

Disclosed and claimed is an improved microbial bioconversion to produce 1,2-dehydro steroids from their corresponding 1,2-saturated derivatives.

8 Claims, No Drawings

Δ¹-DEHYDROGENATION WITH HEAT OR AIR-DRIED B. CYCLOOXIDANS

CROSS REFERENCE TO RELATED APPLICATION

This is a continuation of our co-pending patent application Ser. No. 436,552 filed Oct. 25, 1982 now U.S Pat. No. 4,524,134 which was a continuation-in-part patent application of U.S. patent application Ser. No. 403,949, filed July 30, 1982, now abandoned.

BACKGROUND OF THE INVENTION

The first therapeutic use of corticosteroids was demonstrated in the 1950's with the introduction of cortisone acetate treatment for rheumatoid arthritis. Further studies demonstrated that the insertion of unsaturation into the 1,2 position of hydrocortisone and cortisone caused the resultant steroids, prednisolone and prednisone, to have enhanced potency and to cause less drug-induced salt retention. Subsequently, most other steroids used for the treatment of corticoidresponsive diseases have been synthesized so that they contain a double bond in the 1,2 position of the steroid molecule. In 1977, two U.S. patents were issued which represent new approaches to the synthesis of corticosteroids from sterol precursors. U.S. Pat. No. 4,035,236 covers a process for preparing a 9α-hydroxyandrostenedione via fermentation of sitosterol, stigmasterol, or cholesterol. U.S. Pat. No. 4,041,055 discloses a general process for the synthesis of medically useful corticosteroids from this androstene. Intermediates covered in this chemistry can possess a 3-keto-$\Delta^{4,9(11)}$ configuration.

Following are prior art methods which disclose the bioconversion of 1,2-saturated steroids to their corresponding 1,2-dehydro steroids:

U.S. Pat. No. 2,837,464 "Process for Production of Dienes by Corynebacterium"

Description of 1-dehydrogenation of steroids in fermentation beers by *Arthrobacter* (Corynebacterium) *simplex*.

U.S. Pat. No. 3,360,439 entitled "Process for Preparing 1-dehydro Steroids".

Description of 1-dehydrogenation of steroids by use of *A. simplex* cells pretreated with a lower alkanol or lower alkanone such as acetone before mixing with the substrate and a hydrogen carrier.

Charney, W. and Herzog, H. 1967. *Microbial Transformation of Steroids.* Academic Press, Inc., New York, pp 4–9, 236–261.

Historical background on steroid bioconversions and taxonomic listing of microorganisms known to carry out 1-dehydrogenation. The prior art does not disclose or suggest the subject improved process.

BRIEF SUMMARY OF THE INVENTION

By using air-dried or heat-dried microbial cells that are capable of catalyzing 1-dehydrogenation of steroids, there is obtained a more efficient conversion of 1,2-saturated steroids to their corresponding 1,2-dehydro derivatives than is obtainable by the best known prior art process. This greater efficiency is manifested by (1) a faster rate of conversion while also having much reduced or totally eliminated levels of other steroid modifying enzymes which thus gives better yields of the desired products, and (2) the use of higher substrate levels of certain steroid compounds than is possible in prior art processes. The net effect is that the subject process gives a better yield of desired product than is obtainable by the prior art.

DETAILED DESCRIPTION OF THE INVENTION

Microorganism

The microbes which can be used in the subject process are any of the numerous well-known microbes which are known as 1-dehydrogenators. Such microbes are listed in Charney, W. and Herzog, H. 1967. *Microbial Transformation of Steroids.* Academic Press, Inc., New York.

The bacteria that 1-dehydrogenate steroids fall within two general groups establishes in *Bergey's Manual of Determinative Biology*, 8th edition. The procedure described herein has been successfully demonstrated for species from Arthrobacter and Corynebacterium, genera that are included in "Part 17. Actinomycetes & Related Organisms". The 1-dehydrogenating species of several other general in Part 17, such as Nocardia, Mycobacterium, Streptomyces and Bacterium are probably useful.

Two microorganisms available to the public which are known to 1-dehydrogenation steroids have been demonstrated to lend themselves useful for this type of process. *Bacterium cyclooxydans,* included in U.S. Pat. No. 3,065,146 as a 1-dehydrogenator-ATCC number 12673, has been examined as a useful microorganism. A bacterium that has been used much more extensively for the 1-dehydrogenation of steroids is *Arthrobacter simplex,* ATCC 6946, which is disclosed in U.S. Pat. No. 2,837,464. Thus, much of the following will use this microorganism to exemplify the invention process. It should be understood, however, that the subject process also covers the use of any 1-dehydrogenating microbe.

Growth of the Microorganism—The microorganisms are grown in an aqueous nutrient medium containing:

(a) inorganic compounds such as nitrate or ammonium salts or organic nitrogenous compounds (yeast extract, peptone, cornsteep liquor, etc.) to provide nitrogen for growth.

(b) a carbon and energy source such as carbohydrates and sugar derivatives, oil, fatty acids and their methyl esters, alcohols, amino acids or organic acids.

(c) ions and trace elements such as sodium, potassium, magnesium, phosphate, sulfate, manganese, copper, cobalt, molybdenum, etc. in levels supplied by tap water or by the less refined medium ingredients (such as cornsteep liquor).

The organisms require oxygen present in the atmosphere for growth. The temperature range for growth is 10°-45° C. with an optimum of 28°-37° C. for *A. simplex.* The optimum pH for growth is around neutrality.

Production of the Steroid-1-*Dehydrogenase*—The cells are induced for steroid-1-dehydrogenase activity by the addition of a 1,2 saturated-3-keto-steroid compound such as androsta-4-ene-3,17-dione or cortisone acetate at a level of 0.005% w/v of the medium or greater. In the presence of the inducer, incubation is continued for a period of at least 6 hours before the cells are harvested for drying.

The inducer can be added at any point during the growth cycle. Cultures grown on nutrients such as lard oil will start synthesizing the steroid-1-dehydrogenase rapidly while cultures grown on glucose require substrate depletion before enzyme synthesis will occur. Incubation is continued for a period of 6 or more hours after the inducer is added, then the cells are harvested for drying.

Procedure for Recovering Cells—Cells are separated from the nutrient medium and concentrated by conventional means such as centrifugation, or flocculation, and filtration and ultrafiltration. The separated cells are then dried by placing under reduced pressures at 1°-85° C. (55°-75° preferred), by air drying with heat, or by spray drying, or by tumble drying until a moisture content in the range of about 1 to about 10%. A moisture content of about 5% is preferred. Cells are stored at 5° C. until used for bioconversions. Active dried cells can also be prepared by immobilizing dried cells by standard techniques, such as entrapment within polyacrylamide gel and collagen or covalent coupling of the cells to a polyelectrolyte carrier as described in *Methods in Enzymology*, Vol. XLIV, 1976, Academic Press, Inc., New York, pp 11–317.

Bioconversion Process—The bioconversion is accomplished by exposure of the prepared cells to the steroid substrate. Typically, the cells and steroid are suspended in a weakly buffered aqueous solution with a pH in the range of pH 6—pH 10 with an optimum of pH 7.25–8.5. The amount of cells can range from 0.1–50 g/liter, the steroid is added at a weight ratio of 0.05 to 5.0 (steroid:cells). Cells levels of 8–10 g/liter with 5–10 g/liter steroid are preferred. An exogenous electron carrier is added in catalytic amounts, (e.g., $5 \times 10^{-4}$M menadione) to stimulate the reaction. Useful compounds include menadione (2-methyl-1,4-napthoquinone), phenazine methosulfate, dichlorophenol-indophenol, 1,4-napthoquinone, menadione bisulfite, ubiquinones (Coenzyme Q), and vitamin K-type compounds. The mixtures incubated 0–14 days at a temperature range of 5°–45° C. During incubation, the mixture has access to molecular oxygen and is preferably stirred. The rate of 1-dehydrogenation typically decreases with time. The bioconversion can proceed to 98–99% of completion in less than 24 hours using 10 g/liter substrate.

Examples of the various procedures that can be used include:

(a) Suspension of the steroid and menadione in a weakly buffer aqueous solution, followed by addition of the dried cells. Surfactants such as Tween 80 can be added in low concentration, e.g., 0–5%, to aid in steroid suspension.

(b) Suspension of the cells in an aqueous buffer system, followed by addition of the electron carrier dissolved in ethanol, methanol, acetone (not greater than 5% of final volume). The steroid substrate can be added as a dry powder or dissolved (suspended) in an miscible organic solvent such as dimethyl formamide, ethanol, methanol, acetone, dimethyl sulfoxide, or an immiscible organic solvent such as toluene.

(c) Rehydration of the dried cells in a small volume of buffer followed by the addition of more buffer or of organic solvents. Ethanol, acetone, xylene, butyl acetate, methylene chloride, or toluene, etc. is added to give a final organic solvent content of 0–95% (vol/vol). The steroid and electron carrier are added to initiate the reaction.

Substrate Range—Compounds that are useful in the practice of this invention belong to the 3-keto-$\Delta^4$-androstene and 3-keto-$\Delta^4$-pregnene series of steroids. It is recognized that substrates for the steroid-1-dehydrogenase will have saturation between carbons C1 and C2 of the A ring, and will have a hydroxyl or keto group at position 3 on the A ring. Members of the androstene series include:

(1) androsta-4-ene-3,17-dione and
(2) androsta-4,9(11)-diene-3,17-dione and its 6α-fluoro, 6α-methyl, or 16-methyl derivatives.

Among the steroids of the 3-keto-$\Delta^4$-pregnene series which can be used are:

1. 17α-hydroxypregn-4-ene-20-yn-3-one and its 16-methyl derivatives;
2. 11β,21-dihydroxy-pregn-4,17(20)-diene-3-one and its 6α-methyl derivative;
3. 20-chloro-pregn-4,9(11),17(20)-triene-21-al-3-one;
4. several groups of 3,20-diketo-$\Delta^4$-pregnenes, including
    (a) 11,17,21-trihydroxy compounds, such as hydrocortisone and its 6α-methyl derivative;
    (b) 9β,11β-epoxy-17,21-dihydroxy compounds, such as 9β,11β-epoxy-17,21-dihydroxy-16β-methyl-pregn-4-ene-3,20-dione;
    (c) 3,20-diketo-4,9(11)-pregnedienes such as 17α,21-dihydroxy-pregn-4,9(11)-diene-3,20-dione and its 16α-methyl, 16β-methyl or 16α-hydroxy derivatives or 17α-acetate ester;
    (d) 3,20-diketo-4,9(11), 4,9(11),16-pregnetrienes, such as 21-hydroxy-pregn-4,9(11), 16-triene-3,20-dione and its 6α-fluoro derivative.

The 21-ester derivatives of those steroids containing a 21-hydroxyl group (#2 and #4) serve as substrates also. The preferred 21-esters consist of lower alkyl or aryl groups such as lower fatty acids, e.g. acetic acid, and monocyclic carboxylic acids, e.g., benzoic acid.

The bioconversion products and unconverted substrate can be recovered from the mixtures by conventional means. Steroids are typically recovered by filtration, followed by extraction of the filter cake with an organic solvent, such as acetone or methylene chloride. Alternatively, the whole bioconversion mixture can be extracted by mixing with a water immiscible solvent such as butyl acetate or methylene chloride. The product is then crystallized from the organic solvent.

Following are the results of different bioconversions which demonstrate the superiority of the invention process over prior art processes. The bioconversions were conducted using the conditions detailed above.

EXAMPLE 1

Preparation of dried cells:

*Bacterium cyclo-oxydans* (ATCC 12673) was inoculated into shake flasks containing a medium of cerelose, peptone, and corn steep liquor (6 g/l of each) pH 7.0. The cultures were incubated on a rotary shaker at 28° C. until glucose exhaustion occurred. Cortisone acetate (0.5 g/l) was added at that time and the flasks incubated an additional 16 hrs. The cells were harvested by centrifugation, washed twice with water then placed in a low vacuum oven at 45° C. until dry.

Bioconversion of 6α-methyl hydrocortisone

One-half gram of dried cells, prepared as described above, were rehydrated in 50 ml of 50 mM phosphate buffer pH 7.5 with stirring. Menadione was added to the cell suspension as an ethanolic solution (8.6 mg/ml ethanol) at a level of 0.025 ml/50 ml. The substrate was added as a dimethylformamide (DMF) solution (100 mg 6α-methyl hydrocortisone/ml DMF) to a final bioconversion concentration of 0.5 g/liter. The mixture was incubated at 28° C. with agitation. After 4 hrs incubation, the steroid was 91% converted. The 6α-methyl prednisolone was recovered by conventional means.

EXAMPLE 2 Androsta-1,4,9(11)-triene-3,17-dione Production (a) Preparation of biocatalyst:

*Arthrobacter simplex* (ATCC 6946) was grown in shake flasks in a medium containing 6 g/l glucose, 6 g/l corn steep liquor, and 6 g/l of spray dried lard water. The cultures were incubated at 28° C. on a rotary shaker until glucose depletion occured. At that time, cortisone acetate (0.15 g/l) was added to induce steroid-1-dehydrogenase synthesis. After overnight incubation, the cells were harvested by low speed centrifugation. The cell pellets were placed in a 55° C. low vacuum oven for 24 hr to dry. Twenty-four hours later, the dried material was transferred to an air-tight container and stored at 5° C. until it was needed for a bioconversion.

(b) Bioconversion of androsta-4,9(11)-diene-3,17-dione

Dried cells (10 g/l) were hydrated in 50 mM phosphate buffer pH 7.5 by stirring for 30 minutes. Menadione was then added to cell suspension as a dry powder to a final concentration of 86 mg/liter. Micronized androsta-4,9(11)-diene-3,17-dione was slurried in dimethylformamide and added to the bioconversion mixture at a level of 2.5 g steroid/liter and 2% (v/v) DMF. The mixture was incubated at 31° C. with agitation in the presence of air for 24 hr. After completion of the incubation, androsta-1,4,9(11)-triene-3,17 dione was recovered by conventional means.

EXAMPLE 3

The following steroidal compounds were exposed to dried cells of *A. simplex* in accordance with the conditions described in the preceding example in order to obtain the corresponding 1,2-dehydro derivatives:

| No. | Name |
|-----|------|
| 1. | androsta-4-ene-3,17-dione |
| 2. | 6α-fluoro-androsta-4,9(11)-diene-3,17-dione |
| 3. | 6α-methyl-androsta-4,9(11)-diene-3,17-dione |
| 4. | 16β-methyl-androsta-4,9(11)-diene-3,17-dione |
| 5. | 17β-hydroxypregn-4-ene-20-yn-3-one |
| 6. | 17β-hydroxypregn-4,9(11)-diene-20-yn-3-one |
| 7. | 17α-hydroxy-16β-methyl-pregn-4,9(11)-diene-20-yn-3-one |
| 8. | 11β,21-dihydroxy-pregn-4,17(20)-diene-3-one |
| 9. | 21-acetoxy-11β-hydroxy-pregn-4,17(20)-diene-3-one |
| 10. | 6α-methyl-11β,21-dihydroxy-pregn-4,17(20)-diene-3-one |
| 11. | 20-chloro-pregn-4,9(11),17(20)-triene-21-al-3-one |
| 12. | hydrocortisone |
| 13. | 6α-methyl hydrocortisone |
| 14. | 21-acetoxy-11β,17-dihydroxy-16β-methyl-pregn-4-ene-3,20-dione |
| 15. | 21-acetoxy-9α-fluoro-11β,17-dihydroxy-16β-methyl-pregn-4-ene-3,20-dione |
| 16. | 21-acetoxy-9β,11β-epoxy-17-hydroxy-16β-methyl-pregn-4-ene-3,20-dione |
| 17. | 21-acetoxy-17-hydroxy-pregn-4,9(11)-diene-3,20-dione |
| 18. | 21-acetoxy-16α,17-dihydroxy-pregn-4,9(11)-diene-3,20-dione |
| 19. | 21-acetoxy-17-hydroxy-16α-methyl-pregn-4,9(11)-diene-3,20-dione |
| 20. | 21-benzoyloxy-17-hydroxy-16β-methyl-pregn-4,9(11)-diene-3,20-dione |
| 21. | 21-acetoxy-17-hydroxy-16β-methyl-pregn-4,9(11)-diene-3,20-dione |
| 22. | 21-acetoxy-pregn-4,9(11),16(17)-triene-3,20-dione |
| 23. | 21-acetoxy-6α-fluoro-pregn-4,9(11),16-triene-3,20-dione. |

The corresponding products obtained from the conversions are as follows:

| No. | Products |
|-----|----------|
| 1a | androsta-1,4-diene-3,17-dione |
| 2a | 6α-fluoro-androsta-1,4,9(11)-triene-3,17-dione |
| 3a | 6α-methyl-androsta-1,4,9(11)-triene-3,17-dione |
| 4a | 16β-methyl-androsta-1,4,9(11)-triene-3,17-dione |
| 5a | 17α-hydroxypregn-1,4-diene-20-yn-3-one |
| 6a | 17α-hydroxypregn-1,4,9(11)-triene-20-yn-3-one |
| 7a | 17α-hydroxy-16β-methyl-pregn-1,4,9(11)-triene-20-yn-3-one |
| 8a | 11β,21-dihydroxy-pregn-1,4,17(20)-triene-3-one |
| 9a | 21-acetoxy-11β-hydroxy-pregn-1,4,17(20)-triene-3-one and 11β,21-dihydroxy-pregn-1,4,17(20)-triene-3-one |
| 10a | 6α-methyl-11β,21-dihydroxy-pregn-1,4,17(20)-triene-3-one |
| 11a | 20-chloro-pregn-1,4,9(11),17(20)-tetraene-21-al-3-one |
| 12a | prednisolone |
| 13a | 6α-methyl-prednisolone |
| 14a | 21-acetoxy-11β,17-dihydroxy-16β-methyl-pregn-1,4-diene-3,20-dione and 11β,17,21-trihydroxy-16β-methyl-pregn-1,4-diene-3,20-dione |
| 15a | 21-acetoxy-9α-fluoro-11β,17-dihydroxy-16β-methyl-pregn-1,4-diene-3,20-dione and 9α-fluoro-11β,17,21-trihydroxy-16β-methyl-pregn-1,4-diene-3,20-dione |
| 16a | 21-acetoxy-9β,11β-epoxy-17-hydroxy-16β-methyl-pregn-1,4-diene-3,20-dione and 9β,11β-epoxy-17,21-dihydroxy-16β-methyl-pregn-1,4-diene-3,20-dione |
| 17a | 21-acetoxy-17-hydroxy-pregn-1,4,9(11)-triene-3,20-dione and 17,21-dihydroxy-pregn-1,4,9(11)-triene-3,20-dione |
| 18a | 21-acetoxy-16α,17-dihydroxy-pregn-1,4,9(11)-triene-3,20-dione and 16α,17,21-trihydroxy-pregn-1,4,9(11)-triene-3,20-dione |
| 19a | 21-acetoxy-17-hydroxy-16α-methyl-pregn-1,4,9(11)-triene-3,20-dione and 17,21-dihydroxy-16α-methyl-pregn-1,4,9(11)-triene-3,20-dione |
| 20a | 21-benzoyloxy-17-hydroxy-16β-methyl-pregn-1,4,9(11)-triene-3,20-dione |
| 21a | 21-acetoxy-17-hydroxy-16β-methyl-pregn-1,4,9(11)-triene-3,20-dione and 17,21-dihydroxy-16β-methyl-pregn-1,4,9(11)-triene-3,20-dione |
| 22a | 21-acetoxy-pregn-1,4,9(11),16-tetraene-3,20-dione and 21-hydroxy-pregn-1,4,9(11),16-tetraene-3,20-dione |
| 23a | 21-acetoxy-6α-fluoro-pregn-1,4,9(11),16-tetraene-3,20-dione and 6α-fluoro-21-hydroxy-pregn-1,4,9(11),16-tetraene-3,20-dione. |

EXAMPLE 4

Two different steroids were bioconverted with cells of *A. simplex* in fermentation beer and with dried *A. simplex* cells. After each bioconversion was judged to be finished (as indicated by no further decrease in residual levels), the steroid in the mixture was extracted and isolated to provide yield data for each condition. The following table summarizes those results.

Comparison of Isolation Yields Obtained from Different Types of Bioconversions

| Substrate | Type of Bioconversion | Chemical Yield of Useful Steroid (a) | % Δ' Compound | % Residual | Comment |
|---|---|---|---|---|---|
| [structure: Δ9(11)-androstadienedione] 10 g/liter | Fermentation | 77.2% 1st crop<br>2.8% 2nd crop | 2.6<br>10.4 | 87.4<br>89.6 | Poor 1 dehydrogenation |
|  | Dried Cell | 82.6% 1st crop<br>9.9% 2nd crop | 100.0<br>95.0 | —<br>5.0 |  |
| [structure: 21-acetoxy pregnadienedione] 8 g/liter | Fermentation | 18.1 1st crop<br>No 2nd crop obtained | 59.1 | 40.9 | (b) |
|  | Dried Cells | 79.6% 1st crop<br>No 2nd crop obtained | 97.8 | 2.1 |  |

(a) Useful steroid is defined as either the Δ' compound whioch can be used in furtherr synthesis or the 1,2-dihydro- substrate which can be recycled into another bioconversion to produce product.
(b) Considerable amounts of other undersirable steroid molecules were also recovered.

(b) Considerable amounts of other undesirable steroid molecules were also recovered.

EXAMPLE 5

*Arthrobacter simplex* was grown in a 5-liter "Microferm" fermentor, induced for steroid-1-dehydrogenase synthesis, and harvested by centrifugation. Portions of the recovered cell paste were subjected to two different preparation methods. The first was the procedure disclosed herein which consisted of drying the cells under reduced pressure at 55° C. The second method was the procedure recommended in U.S. Pat. No. 3,360,439 for preparation of acetone-dried cells. Cells were mixed with acetone, harvested and dried at 5° C. under reduced pressure. The dried cell preparations were then used to bioconvert Δ$^{9,11}$-androstenedione in shake flasks at 10 g/liter cells and 10 g/liter steroid.

Comparison of Bioconversion Capacity of *A. simplex* Cells Dried by Different Methods

| Cell Type | Time of Sampling (Hours) | % Residual Substrate | Bioconversion Activity+ (g product formed)/hr/g cells |
|---|---|---|---|
| Acetone-dried | 1 | 98.7 | .013 |
|  | 4 | 95.5 | .011 |
|  | 24 | 84.1* | .007 |
| Heat-dried | 1 | 85.1 | .149 |
|  | 4 | 23.2 | .192 |
|  | 24 | 7.2* | .039 |

+Bioconversion activity is calculated as follows:
$$\frac{\% \text{ product formed} \times \text{g substrate added}}{100} = \text{g product formed}$$
g product formed/hours of incubation/g cells added = activity
*Residual levels did not decrease with further incubation.

EXAMPLE 6

By substituting the following listed substrates for 6α-methyl hydrocortisone in Example 1, or androsta-4,9(11)-diene-3,17-dione in Example 2, there are obtained the corresponding listed products:

Substrates:
1. 21-acetoxy-9α-fluoro-11β,16α,17-trihydroxypregn-4-ene-3,20-dione;
2. 21-acetoxy-6α,9α-difluoro-11β,16α,17-trihydroxypregn-4-ene-3,20-dione-16,17-acetonide;
3. 21-acetoxy-6α-fluoro-11β-hydroxy-16α-methylpregn-4-ene-3,20-dione;
4. 21-acetoxy-6α-fluoro-11β,17-hydroxy-pregn-4-ene-3,20-dione;
5. 21-acetoxy-6α,9α-difluoro-11β,17-dihydroxy-16α-methyl-pregn-4-ene-3,20-dione;
6. 21-acetoxy-9α-fluoro-11β,16α,17-trihydroxypregn-4-ene-3,20-dione-16,17-acetonide;
7. 21-acetoxy-9β,11β-epoxy-6α-fluoro-16α,17-dihydroxy-pregn-4-ene-3,20-dione-16,17-acetonide;
8. 21-acetoxy-9β,11β-epoxy-17α-hydroxy-pregn-4-ene-3,20-dione;
9. 21-acetoxy-9β,11β-epoxy-16α,17-dihydroxypregn-4-ene-3,20-dione-16,17-acetonide;

Products:
1. 21-acetoxy-9α-fluoro-11β,16α,17-trihydroxy-pregn-1,4-diene-3,20-dione and 9α-fluoro-11β,16α,17,21-tetrahydroxy-pregn-1,4-diene-3,20-dione;
2. 21-acetoxy-6α,9α-difluoro-11β,16α,17-trihydroxy-pregn-1,4-diene-3,20-dione-16,17-acetonide and 6α,9α-fluoro-11β,16α,17,21-tetrahydroxy-pregn-1,4-diene-3,20-dione-16,17-acetonide;
3. 21-acetoxy-6α-fluoro-11β-hydroxy-16α-methyl-pregn-1,4-diene-3,20-dione and 6α-fluoro-11β,21-dihydroxy-16α-methyl-pregn-1,4-diene-3,20-dione;
4. 21-acetoxy-6α-fluoro-11β,17-hydroxy-pregn-1,4-diene-3,20-dione and 6α-fluoro-11β,17,21-trihydroxy-1,4-diene-3,20-dione;
5. 21-acetoxy-6α,9α-difluoro-11β,17-dihydroxy-16α-methyl-pregn-1,4-diene-3,20-dione and 6α,9α-difluoro-11β,17,21-trihydroxy-16α-methylpregna-1,4-diene-3,20-dione;
6. 21-acetoxy-9α-fluoro-11β,16α,17-trihydroxy-pregn-1,4-diene-3,20-dione-16,17-acetonide;
7. 21-acetoxy-9β,11β-epoxy-6α-fluoro-16α,17-dihydroxy-pregn-1,4-diene-3,20-dione-16,17-acetonide;
8. 21-acetoxy-9β,11β-epoxy-17α-hydroxy-pregn-1,4-diene-3,20-dione and 9β,11β-epoxy-17α,21-dihydroxy-pregn-1,4-diene-3,20-dione;
9. 21-acetoxy-9β,11β-epoxy-16α,17-dihydroxy-pregn-1,4-diene-3,20-dione-16,17-acetonide.

EXAMPLE 7

Bioconversion of 11β-hydroxy-androsta-4-ene-3,17-dione.

One gram of dried *A. simplex* cells, prepared as described in Example 2, was resuspended in 100 ml 50 mM phosphate buffer pH 7.5. Menadione, dissolved in 3A ethanol, was added to a final concentration of 86 mg/liter. One-half gram of 11β-hydroxy-androstenedione was added to the flask. The mixture was incubated on a rotary shaker at 31° C. When sampled after 1-day's incubation, two products were observed by thin layer chromatography of a methylene chloride extract. Approximately 95% of the steroid was present as 11β-hydroxy-androsta-1,4-diene-3,17-dione. The remainder was unconverted substrate.

EXAMPLE 8

Upon following the conditions of Example 7, the following androstenedione derivatives that are modified at the C-11 position can be 1-dehydrogenated to the products shown:
Substrate→Product
(1) 11β-hydroxy-16β-methyl-androsta-4-ene-3,17-dione→11β-hydroxy-16β-methyl-androsta-1,4-diene-3,17-dione
(2) 11β-hydroxy-16α-methyl-androsta-4-ene-3,17-dione→11β-hydroxy-16α-methyl-androsta-1,4-diene-3,17-dione
(3) 6α-fluoro-11β-hydroxy-androsta-4-ene-3,17-dione→6α-fluoro-11β-hydroxy-androsta-1,4-diene-3,17-dione
(4) 6α-methyl-11β-hydroxy-androsta-4-ene-3,17-dione→6α-methyl-11β-hydroxy-androsta-1,4-diene-3,17-dione
(5) 11α-hydroxy-androsta-4-ene-3,17-dione→11α-hydroxy-androsta-1,4-diene-3,17-dione
(6) androsta-4-ene-3,11,17-trione→androsta-1,4-diene-3,11,17-trione.

The utility of 1,2-dehydro steroids is well known. For example, see U.S. Pat. No. 3,284,447, which discloses the utility of $\Delta^{1,4,9(11)}$ pregnetrienes in the synthesis of diurectic corticosteroids substituted at carbon 16. U.S. Pat. No. 4,041,055 discloses a process for the synthesis of corticosteroids from $\Delta^{1,4}$-androstenedione derivatives, demonstrating the utility of 1,2-dehydroandrostenes as important intermediates in the production of medically useful steroids.

We claim:
1. A process for preparing a 1,2-dehydro-$\Delta^4$-3-keto steroid selected from the group consisting of

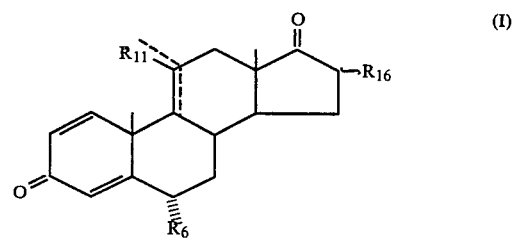

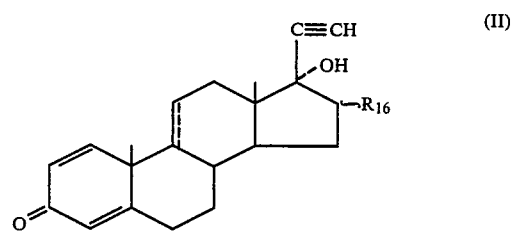

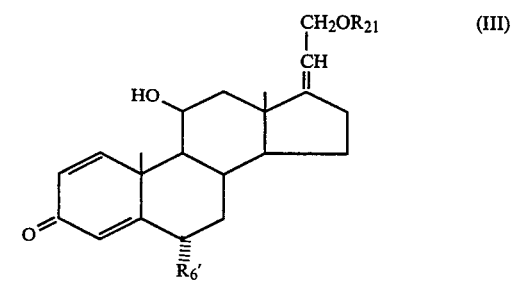

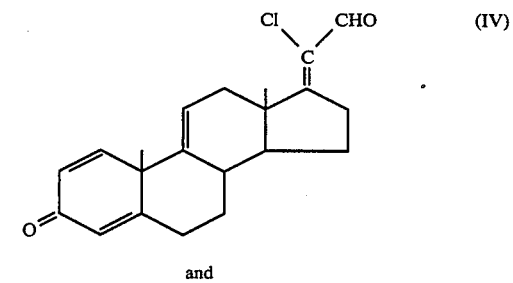

and

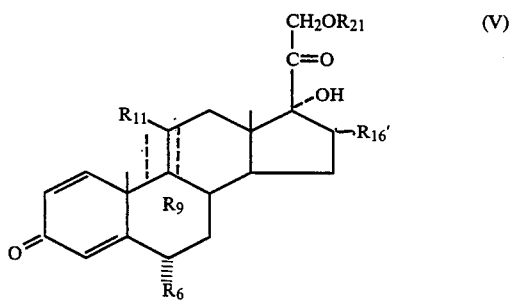

where $R_6$ is a hydrogen or fluorine atom or methyl;
$R_6'$ is a hydrogen atom or methyl group;
$R_9$ is nothing, a hydrogen, fluorine or oxygen atom which makes the C-ring
  (a) $\Delta^{9(11)}$ when $R_9$ is nothing and
  (b) $9\beta,11\beta$-epoxide when $R_9$ is an oxygen atom;
$R_{11}$ is a hydrogen or oxygen atom, two hydrogen atoms, or $\alpha$- or $\beta$-hydroxyl group which makes the C-ring
  (a) $\Delta^{9(11)}$ when $R_{11}$ is a hydrogen atom,
  (b) $9\beta,11\beta$-epoxide when $R_{11}$ is an oxygen atom and ---- between $C_{11}$ and $R_{11}$ is a single bond, and
  (c) a ketone when $R_{11}$ is an oxygen atom and ---- between $C_{11}$ and $R_{11}$ is a double bond;
~ indicates that the attached group can be in either the $\alpha$ or $\beta$ configuration;
---- is a single or double bond;
$R_{11}'$ is a $\beta$-hydroxyl group, an oxygen atom (11-ketone), or hydrogen atom ($\Delta^{9(11)}$);
$R_{16}$ is a hydrogen atom or methyl group;
$R_{16}'$ is a hydrogen atom, methyl or hydroxyl group, when $R_{16}'$ is an $\alpha$-hydroxyl group the $16\alpha$ and $17\alpha$-hydroxyl groups can be in the form of an acetonide;
$R_{21}$ is a hydrogen atom or $-OC-OR_{21}'$;
$R_{21}'$ is methyl, ethyl, or phenyl which comprises exposing the corresponding 1,2-saturated-$\Delta^4$-3-keto steroid to air-dried or heat-dried cells of Bacterium cyclooxydans having a moisture content of about 1 to about 10% where the cells are dried in the absence of an organic solvent.

2. A process according to claim 1 where the 1,2-dehydro-$\Delta^4$-3-keto steroid is selected from the group consisting of
1. 6$\alpha$-methylprednisolone
2. Androsta-1,4,9(11)-triene-3,17-dione
3. androsta-1,4-diene-3,17-dione
4. 6$\alpha$-fluoroandrosta-1,4,9(11)-triene-3,17-dione
5. 6$\alpha$-methylandrosta-1,4,9(11)-triene-3,17-dione
6. 16$\beta$-methylandrosta-1,4,9(11)-triene-3,17-dione
7. 17$\beta$-hydroxypregna-1,4-diene-20-yn-3-one
8. 17$\alpha$-hydroxypregna-1,4,9(11)-triene-20-yn-3-one
9. 17$\beta$-hydroxy-16$\beta$-methylpregna-1,4,9(11)-triene-20-yn-3-one
10. 11$\beta$,21-dihydroxypregna-1,4,17(20)-trien-3-one
11. 21-acetoxy-11$\beta$-hydroxypregna-1,4,17(20)-trien-3-one
12. 6$\alpha$-methyl-11$\beta$,21-dihydroxypregna-1,4,17(20)-trien-3-one
13. 20-chloropregna-1,4,9(11),17(20)-tetraen-21-al-3-one
14. prednisolone
15. 21-acetoxy-11$\beta$,17-dihydroxy-16$\beta$-methylpregna-1,4-diene-3,20-dione
16. 11$\beta$,17,21-trihydroxy-16$\beta$-methylpregna-1,4-diene-3,20-dione
17. 21-acetoxy-9$\alpha$-fluoro-11$\beta$,17-dihydroxy-16$\beta$-methylpregna-1,4-diene-3,20-dione
18. 9$\alpha$-fluoro-11$\beta$,17,21-trihydroxy-16$\beta$-methylpregna-1,4-diene-3,20-dione
19. 21-acetoxy-9$\beta$,11$\beta$-epoxy-17-hydroxy-16$\beta$-methylpregna-1,4-diene-3,20-dione
20. 9$\beta$,11$\beta$-epoxy-17,21-dihydroxy-16$\beta$-methylpregna-1,4-diene-3,20-dione
21. 21-acetoxy-17-hydroxypregna-1,4,9(11)-triene-3,20-dione
22. 17,21-dihydroxypregna-1,4,9(11)-triene-3,20-dione
23. 21-acetoxy-16$\alpha$,17-dihydroxypregna-1,4,9(11)-triene-3,20-dione
24. 16$\alpha$,17,21-trihydroxypregna-1,4,9(11)-triene-3,20-dione
25. 21-acetoxy-17-hydroxy-16$\alpha$-methylpregna-1,4,9(11)-triene-3,20-dione
26. 17,21-dihydroxy-16$\alpha$-methylpregna-1,4,9(11)-triene-3,20-dione
27. 21-benzoyloxy-17-hydroxy-16$\beta$-methylpregna-1,4,9(11)-triene-3,20-dione
28. 21-acetoxy-17-hydroxy-16$\beta$-methylpregna-1,4,9(11)-triene-3,20-dione
29. 17,21-dihydroxy-16$\beta$-methylpregna-1,4,9(11)-triene-3,20-dione
30. 21-acetoxypregna-1,4,9(11),16-tetraene-3,20-dione
31. 21-hydroxypregna-1,4,9(11),16-tetraene-3,20-dione
32. 21-acetoxy-6$\alpha$-fluoropregna-1,4,9(11),16-tetraene-3,20-dione
33. 6$\alpha$-fluoro-hydroxypregna-1,4,9(11),16-tetraene-3,20-dione
34. 21-acetoxy-9$\alpha$-fluoro-11$\beta$,16$\alpha$,17-trihydroxypregna-1,4-diene-3,20-dione
35. 9$\alpha$-fluoro-11$\beta$,16$\alpha$,17,21-tetrahydroxypregna-1,4-diene-3,20-dione
36. 21-acetoxy-6$\alpha$,9$\alpha$-difluoro-11,$\beta$,16$\alpha$,17-trihydroxypregna-1,4-diene-3,20-dione-16,17-acetonide
37. 6$\alpha$,9$\alpha$-fluoro-11$\beta$,16$\alpha$,17,21-tetrahydroxypregna-1,4-diene-3,20-dione 16,17-acetonide
38. 21-acetoxy-6$\alpha$-fluoro-11$\beta$-hydroxy-16$\alpha$-methylpregna-1,4-diene-3,20-dione
39. 6$\alpha$-fluoro-11$\beta$,21-dihydroxy-16$\alpha$-methylpregna-1,4-diene-3,20-dione
40. 21-acetoxy-6$\alpha$-fluoro-11$\beta$,17-hydroxypregna-1,4-diene-3,20-dione
41. 6$\alpha$-fluoro-11$\beta$,17,21-trihydroxy-1,4-diene-3,20-dione
42. 21-acetoxy-6$\alpha$,9$\alpha$-difluoro-11$\beta$,17-dihydroxy-16$\alpha$-methylpregna-1,4-diene-3,20-dione
43. 6$\alpha$,9$\alpha$-difluoro-11$\beta$,17,21-trihydroxy-16$\alpha$-methylpregna-1,4-diene-3,20-dione
44. 21-acetoxy-9$\alpha$-fluoro-11$\beta$,16$\alpha$,17-trihydroxypregna-1,4-diene-3,20-dione 16,17-acetonide
45. 21-acetoxy-9$\beta$,11$\beta$-epoxy-6$\alpha$-fluoro-16$\alpha$,17-dihydroxypregna-1,4-diene-3,20-dione 16,17-acetonide
46. 21-acetoxy-9$\beta$,11$\beta$-epoxy-17-hydroxypregna-1,4-diene-3,20-dione
47. 9$\beta$,11$\beta$-epoxy-17$\alpha$,21-dihydroxypregna-1,4-diene-3,20-dione
48. 21-acetoxy-9$\beta$,11$\beta$-epoxy-16$\alpha$,17-dihyroxypregna-1,4-diene-3,20-dione 16,17-acetonide
49. 11$\beta$-hydroxyandrosta-1,4-diene-3,17-dione
50. 11$\beta$-hydroxy-16$\beta$-methylandrosta-1,4-diene-3,17-dione
51. 11$\beta$-hydroxy-16$\alpha$-methylandrosta-1,4-diene-3,17-dione
52. 6$\alpha$-fluoro-11$\beta$-hydroxyandrosta-1,4-diene-3,17-dione
53. 6$\alpha$-methyl-11$\beta$-hydroxyandrosta-1,4-diene-3,17-dione
54. 11$\alpha$-hydroxyandrosta-1,4-diene-3,17-dione
55. androsta-1,4-diene-3,11,17-trione.

3. A process according to claim 2 where the 1,2-dehydro-$\Delta^4$-3-keto steroid is selected from the group consisting of 6$\alpha$-methylprednisolone, androsta-1,4,9(11)-triene-3,17-dione, androsta-1,4-diene-3,17-dione, 16$\beta$-methylandrosta-1,4,9(11)-triene-3,17-dione, prednisolone, 17,21-dihydroxypregna-1,4,9(11)-triene-3,20-dione 21-acetoxy-16$\alpha$,17-dihydroxypregna-1,4,9(11)- triene-3,20-dione, 16α,17,21-trihydroxypregna-1,4,9(11)-triene-3,20-dione, 21-acetoxypregna-1,4,9(11), 16-tetraene-3,20-dione, 21-hydroxypregna-1,4,9(11), 16-tetraene-3,20-dione, 21-acetoxy-6α-fluoropregna-1,4,9(11), 16-tetraene-3,20-dione, 6α-fluoro-11β,17,21-trihydroxy-1,4-diene-3,20-dione, 11β-hydroxyandrosta-1,4-diene-3,17-dione, 11β-hydroxy-16β-methylandrosta-1,4-diene-3,17-dione.

4. A process according to claim 2 where the 1,2-dehydro-Δ$^4$-3-keto steroid is selected from the group consisting of 21-acetoxy-9α-fluoro-11β,17-dihydroxy-16β-methylpregna-1,4-diene-3,20-dione, 9α-fluoro-11β,17,21-trihydroxy-16β-methylpregna-1,4-diene-3,20-dione, 21-acetoxy-17-hydroxy-16α-methylpregna-1,4,9(11)-triene-3,20-dione, 17,21-dihydroxy-16α-methylpregna-1,4,9(11)-triene-3,20-dione, 21-acetoxy-9α-fluoro-11β,16α,17-trihydroxypregna-1,4-diene-3,20-dione, 9α-fluoro-11β,16α,17,21-tetrahydroxypregna-1,4-diene-3,20-dione, 21-acetoxy-6α,9α-difluoro-11β,16α,17-trihydroxypregna-1,4-diene-3,20-dione-16,17-acetonide, 6α,9α-fluoro-11β,16α,17,21-tetrahydroxypregna-1,4-diene-3,20-dione 16,17-acetonide, 21-acetoxy-6α-fluoro-11β-hydroxy-16α-methylpregna-1,4-diene-3,20-dione, 6α-fluoro-11β,21-dihydroxy-16α-methylpregna-1,4-diene-3,20-dione, 21-acetoxy-6α-fluoro-11β,17-hydroxypregna-1,4-diene-3,20-dione, 21-acetoxy-6α,9α-difluoro-11β,17-dihydroxy-16α-methylpregna-1,4-diene-3,20-dione, 21-acetoxy-9α-fluoro-11β,16α,17-trihydroxy-pregna-1,4-diene-3,20-dione 16,17-acetonide, 21-acetoxy-9β,11β-epoxy-6α-fluoro-16α,17-dihydroxypregna-1,4-diene-3,20-dione 16,17-acetonide, 21-acetoxy-9β,11β-epoxy-16-hydroxypregna-1,4-diene-3,20-dione, 9β,11β-epoxy-16α,21-dihydroxypregna-1,4-diene-3,20-dione, 21-acetoxy-9β,11β-epoxy-16α,17-dihydroxypregna-1,4-diene-3,20-dione 16,17-acetonide, 11β-hydroxy-16α-methylandrosta-1,4-diene-3,27-dione, 11α-hydroxyandrosta-1,4-diene-3,17-dione, androsta-1,4-diene-3,11,17-trione.

5. A process according to claim 1 which is performed in the presence of an exogenous electron carrier.

6. A process according to claim 5, where the exogenous electron carrier is selected from the group consisting of menadione, phenazine methosulfate, dichlorophenolindophenol, 1,4-naphthoquinone, menadione bisulfite, ubiquinones (Coenzyme Q), or vitamin K-type compounds.

7. A process according to claim 6 where the exogenous electron carrier is selected from the group consisting of menadione, phenazine methosulfate, dichlorophenolindophenol, 1,4-naphthoquinone or menadione bisulfite.

8. A process according to claim 7 where the exogenous electron carrier is menadione.

* * * * *

UNITED STATES PATENT AND TRADEMARK OFFICE
CERTIFICATE OF CORRECTION

PATENT NO. : 4,704,358

DATED : November 3, 1987

INVENTOR(S) : L. A. Kominek, et al

It is certified that error appears in the above-identified patent and that said Letters Patent is hereby corrected as shown below:

Column 10, lines 62-64: " 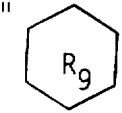 " should read -- 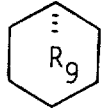 --.

Column 11, line 43: "8. 17α" should read --8. 17β--.
Column 11, line 44: "9. 17β" should read --9. 17α--.
Column 12, line 68: "dione" should read --dione,--.

Signed and Sealed this

Sixth Day of September, 1988

Attest:

DONALD J. QUIGG

Attesting Officer

Commissioner of Patents and Trademarks